United States Patent [19]

Brown et al.

[11] Patent Number: 5,229,513
[45] Date of Patent: Jul. 20, 1993

[54] METHOD FOR PREPARING SUBSTITUTED DICHLOROTRIAZINES

[75] Inventors: Sterling B. Brown; Thomas J. Stanley, both of Schenectady, N.Y.

[73] Assignee: General Electric Company, Schenectady, N.Y.

[21] Appl. No.: 946,115

[22] Filed: Sep. 17, 1992

[51] Int. Cl.$^5$ ............................................ C07D 251/26
[52] U.S. Cl. .................................................. 544/218
[58] Field of Search ........................................ 544/218

[56] References Cited

U.S. PATENT DOCUMENTS

| | | | |
|---|---|---|---|
| 4,104,250 | 8/1978 | Boyer | 544/218 |
| 4,271,299 | 6/1981 | Hentschel et al. | 544/218 |
| 4,284,772 | 8/1981 | Hoentjen et al. | 544/218 |
| 4,895,945 | 1/1990 | Brown et al. | 544/218 |

Primary Examiner—John M. Ford
Attorney, Agent, or Firm—William H. Pittman

[57] ABSTRACT

Substituted dichlorotriazines are prepared by the reaction of a suitable hydroxy compound with cyanuric chloride in a substantially non-polar organic solvent, in the presence of an aqueous alkali metal hydroxide solution having a concentration in the range of about 1–20% by weight and a phase transfer catalyst. The phase transfer catalyst employed is a tetraalkylammonium or tetraalkylphosphonium salt free from aromatic substituents and wherein the alkyl groups contain 3-5 carbon atoms. Hydrophilic phase transfer catalysts, in which the alkyl groups contain up to about 5 carbon atoms, are preferred.

20 Claims, No Drawings

METHOD FOR PREPARING SUBSTITUTED DICHLOROTRIAZINES

This invention relates to the preparation of substituted dichlorotriazines, and more particularly to an improved method for their preparation which employs a phase transfer catalyst.

The reaction or cyanuric chloride with alcohols and phenols is well known in the art. Depending on the molar ratios of reactants employed, the products may be principally mono-, di- or trisubstituted triazines in which the substituents are alkoxy or aryloxy groups, with any remaining substitutable positions being satisfied by chlorine atoms.

In recent years, monochlorotriazines containing two different substituents have become of increasing interest by reason of their capability of reaction with hydroxy-terminated polymers to form functionalized polymers, which in turn can be converted to copolymers. For example, U.S. Pat. No. 4,895,945 describes the preparation of such compounds as 2-chloro-4-mesitoxy-6-glycidoxy-1,3,5-triazine and the use of such compounds as capping agents for polyphenylene ethers. Similar triazines containing a chloro- or phosphatoalkoxy group are disclosed in copending, commonly owned application Ser. No. 07/654,444, now U.S. Pat. No. 5,159,075.

In the preparation of compounds of this type, cyanuric chloride is an initial reactant and two separate reactions are involved. The first is most often with a phenol free from displaceable substituents such as chloro, epoxy or phosphato groups, to produce a simple monosubstituted dichlorotriazine (hereinafter sometimes simply "dichlorotriazine"). Inevitably, however, further reaction to form the disubstituted monochlorotriazine (hereinafter sometimes "by-product monochlorotriazine") occurs to some extent. In addition, serious emulsion formation between the organic and aqueous layers of the reaction mixture is often a problem.

The second reaction is between the dichlorotriazine and a hydroxy compound containing a displaceable substituent, such as glycidol, 2-chloroethanol or 2-hydroxyethyl diethyl phosphate, to form the desired monochlorotriazine containing two different substituents, only one of which is displaceable. Upon capping of a polymer with the monochlorotriazine formed in said second reaction, the displaceable group remains available for copolymer formation. To the extent that by-product monochlorotriazine has been formed in the first reaction, it will compete with the compound containing the displaceable substituent in the capping reaction, producing an essentially inert polymer incapable of further reaction to form copolymer.

Thus, it is desired to minimize the proportion of by-product monochlorotriazine in the reaction with cyanuric chloride, and also to minimize emulsion formation. These objectives are achieved by the present invention.

Accordingly, the invention is a method for preparing a monoaryloxydichlorotriazine which comprises contacting, at a temperature in the range of about 0°-60° C., (A) at least one monohydroxyaromatic compound with (B) cyanuric chloride, in the presence of (C) a substantially non-polar organic solvent, (D) a phase transfer catalyst comprising at least one tetraalkylammonium or tetraalkylphosphonium salt free from aromatic substituents and wherein the alkyl groups contain 3-5 carbon atoms, and (E) an aqueous alkali metal hydroxide solution having a concentration in the range of about 1-20% by weight; the molar ratio of reagent A to said cyanuric chloride being in the range of about 1.00-1.05:1.

Reagent A in the method of this invention is a monohydroxyaromatic compound or alkali metal salt thereof, or mixture of such compounds. Such compounds are exemplified by phenol, 2,6-xylenol, mesitol (i.e., 2,4,6-trimethylphenol), 1-naphthol and 2-naphthol. Preferred are monocyclic monohydroxyaromatic compounds (hereinafter sometimes designated "phenols"), and especially those containing alkyl substituents including mesitol and 2,6-xylenol.

Reagent B is cyanuric chloride, also known as 2,4,6-trichloro-1,3,5-triazine.

Also present is (C) a substantially non-polar organic solvent, The preferred solvents are substantially water-immiscible liquids such as chloroform, methylene chloride, toluene, xylene and chlorobenzene. Aromatic liquids are preferred, with aromatic hydrocarbons and especially toluene being most preferred.

Phase transfer catalysts useful as component D are known in the art. Such catalysts are believed to function by facilitating transfer of a reagent which is normally substantially insoluble in the aqueous or organic phase of a heterogeneous reaction mixture across the phase interface into said phase. The phase transfer catalysts used according to the invention are tetraalkylammonium and tetraalkylphosphonium salts (e.g., halides, bisulfates) free from aromatic substituents, wherein the alkyl groups contain 3-5 carbon atoms.

Two particular classes of phase transfer catalysts are contemplated in accordance with the present invention: hydrophilic catalysts, which are predominantly soluble in and compatible with the aqueous phase, and organophilic catalysts, which have that relationship with the organic phase. Hydrophilic catalysts are generally characterized by the presence of alkyl groups containing up to about 5 carbon atoms and the absence of larger alkyl groups, while organophilic catalysts typically contain at least one alkyl group having about 8-15 carbon atoms. The hydrophilic catalysts are strongly preferred according to the present invention, by reason of their high selectivity for monosubstitution to form the dichlorotriazine.

The final reagent is (E) an aqueous alkali metal hydroxide solution (hereinafter sometimes "base solution"). The preferred alkali metal hydroxides are sodium hydroxide and potassium hydroxide, with sodium hydroxide being preferred because of its availability and effectiveness.

The concentration of the base solution is in the range of about 1-20% and preferably 1-15% by weight. This is substantially less concentrated than the solutions typically employed according to the prior art, which frequently had concentrations on the order of 50%. It is believed that one effect of the use of more dilute solutions is that the additional water assists in maintaining the temperature within the desired range by absorbing the heat evoked in the exothermic reaction. Typical molar ratios of base to cyanuric chloride are in the range of about 1.05-2.5:1.

In the practice of the method of this invention, contact between the reagents is typically effected with agitation to ensure intimate mixing. It is preferred to add reagent A to the cyanuric chloride or to bring the two simultaneously into contact, thereby preventing the existence of a molar excess of reagent A at any time and promoting monosubstitution rather than di- or trisubstitution. The cyanuric chloride and phase transfer catalyst are ordinarily premixed with the organic solvent.

Most often, reagent A and the base solution are separately added to the cyanuric chloride, with reagent A being introduced simultaneously with or immediately after the cyanuric chloride and the base solution being subsequently added, most often as rapidly as possible. It is also within the scope of the invention, however, to premix reagent A with the base solution. This typically results in the formation of an alkali metal salt of said phenol. The resulting aqueous solution, containing any unreacted base and said alkali metal salt, may then be introduced into the vessel containing the cyanuric chloride.

Another important factor is the molar ratio of reagent A to cyanuric chloride, which should be in the range of about 1.00–1.05:1. Incomplete conversion to dichlorotriazine will occur if a ratio lower than 1:1 is employed, and ratios greater than 1.05:1 tend to promote disubstitution to form the by-product monochlorotriazine. Ratios of about 1.00–1.03:1 are preferred. The phase transfer catalyst is employed in an amount effective to catalyze the heterogeneous reaction, most often about 0.5–5 mole percent based on cyanuric chloride. The reaction temperature employed is in the range of about 0°–60° and preferably about 20°–50° C.

The course of the substitution reaction can be followed by liquid chromatography. It is usually found that the reaction is essentially complete within about 5–30 minutes, depending on reaction scale. Upon completion, the dichlorotriazine product is dissolved in the organic layer of the reaction mixture and said layer may be separated and employed in further reactions, such as conversion to a functionalized monochlorotriazine. If isolation of the dichlorotriazine is desired, it may be accomplished by conventional means such as evaporation of the solvent or precipitation with a non-solvent; however, such isolation is seldom necessary.

The invention is illustrated by the following examples. The phase transfer catalysts employed in these examples and the controls are identified as follows; the first five are within the scope of the invention and the last three were employed for comparison purposes.

MTAAC—"Adogen 464", a methyltrialkylammonium bromide in which the alkyl groups contain 8–10 carbon atoms.
TBABS—Tetra-n-butylammonium bisulfate.
TBAB—Tetra-n-butylammonium bromide.
TBAC—Tetra-n-butylammonium chloride.
TBPB—Tetra-n-butylphosphonium bromide.
HTMAB—Hexadecyltrimethylammonium bromide.
BTEAC—Benzyltriethylammonium chloride.
TMAB—Tetramethylammonium bromide.

EXAMPLES 1–6

A number of 400-ml. beakers were charged with 14 grams (75.9 mmol.) of cyanuric chloride, 10.42 grams (76.5 mmol.) of mesitol, 1 gram of naphthalene as an internal standard, various phase transfer catalysts in the amount of 2 mole percent based on cyanuric chloride and 86 grams of toluene. The mixtures were stirred rapidly and, in Example 2, cooled with an ice-water bath; the temperatures of the mixtures were determined with a thermocouple.

There was added in one portion, with continued stirring, a solution of 3.36 grams of sodium hydroxide in enough water to provide a total volume of 100 ml. (i.e., 1.1 moles of sodium hydroxide per mole of cyanuric chloride), whereupon an exotherm was noted. A timer was started when sodium hydroxide addition was completed; stirring was continued as 1-ml. aliquots of the reaction mixture were taken at 30, 80 and 300 seconds, quenched in carbon dioxide-saturated water and analyzed by liquid chromatography to determine the percent conversion (i.e., the proportion of total dichlorotriazine and by-product monochlorotriazine as a percentage of cyanuric chloride employed) and selectively for dichlorotriazine (i.e., molar ratio of dichlorotriazine to by-product monochlorotriazine).

The results are given in Table I. In the examples, phase transfer catalysts as defined for the present invention were used. Comparison was made with controls in which no phase transfer catalyst or catalysts not within the scope of the invention, by reason of number of carbon atoms or substituents thereon, were employed.

TABLE I

| Example | Phase transfer catalyst | Temperature, °C. | Conversion, % (selectivity) | | |
|---|---|---|---|---|---|
| | | | 30 sec. | 80 sec. | 300 sec. |
| 1 | MTAAC | 27–44 | 94(12) | 88(12) | 92(13) |
| 2 | MTAAC | 5–31 | 93(12) | 92(14) | 92(12) |
| 3 | TBABS | 26–39 | 80(31) | 8831) | 96(23) |
| 4 | TBAB | 25–42 | 81(34) | 95(34) | 99(30) |
| 5 | TBAC | 26–41 | 90(33) | 92(31) | 95(27) |
| 6 | TBPB | 26–44 | 95(25) | 95(25) | 97(25) |
| Control 1 | — | 27–41 | 68(28) | 81(31) | 87(22) |
| Control 2 | HTMAB | 25–45 | 81(5) | 80(5) | 80(5) |
| Control 3 | BTEAC | 26–39 | 56(11) | 71(11) | 87(14) |
| Control 4 | TMAB | 26–41 | 56(35) | 72(33) | 88(22) |

The results in Table I show that substantially higher conversions are obtained with the use of the phase transfer catalysts employed in the invention than with other catalysts or no catalyst. In addition, selectively is substantially higher and conversion comparable, at least at 300 seconds, with the employment of a hydrophilic phase transfer catalyst (Examples 3–6) than with an organophilic one (Examples 1–2). A comparison of Examples 1 and 2 demonstrates that there is no substantial advantage in operating at low temperature.

Various reaction mixtures were poured into a separatory funnel 5–15 minutes after base addition was complete. In each instance except Control 2, there was clean separation of the aqueous and organic layers with no tendency toward formation of an emulsion. In Control 2, an emulsion formed which was essentially impossible to break.

EXAMPLES 7–9

The procedure of Example 4 was repeated, employing base solutions of various concentrations. The results are given in Table II.

TABLE II

| Example | Base soln., % | Temperature, °C. | Conversion, % (selectivity) | | |
|---|---|---|---|---|---|
| | | | 30 sec. | 80 sec. | 300 sec. |
| 7 | 3.4 | 25–42 | 81(34) | 95(34) | 99(30) |
| 8* | 6.8 | 26–44 | — | — | 97(27) |
| 9 | 17 | 25–59 | 95(19) | 95(18) | 92(18) |
| Control 5 | 50 | 25–60 | 48(8) | 71(9) | 84(7) |

*2.2 moles of base per mole of cyanuric chloride.

The results in Table II show the desirability of using base solution having a concentration of 1–20%, as opposed to 50% which results in both lower conversion and lower selectivity. The advantages of a base concentration less than 15%, from the standpoint of high selectivity, is also shown.

EXAMPLE 10

Various runs were made following the procedure of Example 4, but scaling up the reaction to 18.4 kg. of cyanuric chloride with other components in proportion. The average addition time of the sodium hydroxide solution was 8.5 minutes. Conversions of 90-96% and selectivities of 22-24 were observed in time periods from 8 to 27 minutes, with yields of dichlorotriazine (i.e., moles thereof as a percentage of moles of starting cyanuric chloride) being in the range of 85-90%.

What is claimed is:

1. A method for preparing a monoaryloxydichlorotriazine which comprises contacting, at a temperature in the range of about 0°-60° C., (A) at least one monohydroxyaromatic compound with (B) cyanuric chloride, in the presence of (C) a substantially non-polar organic solvent, (D) a phase transfer catalyst comprising at least one tetraalkylammonium or tetraalkylphosphonium salt free from aromatic substituents and wherein the alkyl groups contain 3-15 carbon atoms, and (E) an aqueous alkali metal hydroxide solution having a concentration in the range of about 1-20% by weight; the molar ratio of reagent A to said cyanuric chloride being in the range of about 1.00-1.05:1.

2. A method according to claim 1 wherein reagent A is a monocyclic monohydroxyaromatic compound.

3. A method according to claim 2 wherein the molar ratio of reagent A to cyanuric chloride is in the range of about 1.00-1.03:1.

4. A method according to claim 3 wherein the organic solvent is an aromatic liquid.

5. A method according to claim 4 wherein the phase transfer catalyst is a hydrophilic catalyst.

6. A method according to claim 5 wherein the alkali metal hydroxide is sodium hydroxide.

7. A method according to claim 5 wherein the concentration of the alkali metal hydroxide solution is in the range of about 1-15% by weight.

8. A method according to claim 7 wherein the reaction temperature is in the range of about 20°-50° C.

9. A method according to claim 7 wherein the reagents A and E are separately added to the cyanuric chloride.

10. A method according to claim 7 wherein reagents A and E are premixed and the resulting aqueous solution is added to the cyanuric chloride.

11. A method according to claim 7 wherein the amount of phase transfer catalyst is about 1-5 mole percent based on cyanuric chloride.

12. A method according to claim 7 wherein the alkyl groups in the phase transfer catalyst contain up to about 5 carbon atoms.

13. A method according to claim 12 wherein the phase transfer catalyst is tetra-n-butylammonium bromide.

14. A method according to claim 12 wherein the phase transfer catalyst is tetra-n-butylammonium chloride.

15. A method according to claim 12 wherein the phase transfer catalyst is tetra-n-butylammonium bisulfate.

16. A method according to claim 12 wherein the phase transfer catalyst is tetra-n-butylphosphonium bromide.

17. A method according to claim 7 wherein reagent A is mesitol.

18. A method according to claim 7 wherein reagent A is 2,6-xylenol.

19. A method according to claim 7 wherein the organic solvent is an aromatic hydrocarbon.

20. A method according to claim 19 wherein the organic solvent is toluene.

* * * * *